(12) United States Patent
Jaster et al.

(10) Patent No.: US 10,739,264 B1
(45) Date of Patent: Aug. 11, 2020

(54) SOIL IMAGING PROBE AND METHOD OF PROCESSING SOIL IMAGE TO DETECT HYDROCARBON CONTAMINATION

(71) Applicant: Kejr, Inc., Salina, KS (US)

(72) Inventors: Ben Jaster, Salina, KS (US); Thomas M. Christy, Salina, KS (US); Blake G. Slater, Salina, KS (US); Steven M. Colgrove, Salina, KS (US)

(73) Assignee: Kejr Inc., Salina, KS (US)

( * ) Notice: Subject to any disclaimer, the term of this patent is extended or adjusted under 35 U.S.C. 154(b) by 0 days.

(21) Appl. No.: 16/526,392

(22) Filed: Jul. 30, 2019

Related U.S. Application Data

(62) Division of application No. 15/269,159, filed on Sep. 19, 2016, now Pat. No. 10,371,637.

(60) Provisional application No. 62/220,644, filed on Sep. 18, 2015.

(51) Int. Cl.
*G01N 21/64* (2006.01)
*G01V 8/10* (2006.01)
*G01N 21/94* (2006.01)

(52) U.S. Cl.
CPC ......... *G01N 21/6456* (2013.01); *G01N 21/94* (2013.01); *G01V 8/10* (2013.01); *G01N 2201/12* (2013.01)

(58) Field of Classification Search
CPC ............... G01N 21/6456; G01N 21/94; G01N 2201/12; G01V 8/10
USPC ...................................................... 250/256
See application file for complete search history.

(56) References Cited

U.S. PATENT DOCUMENTS

| | | | | |
|---|---|---|---|---|
| 5,128,882 A | * | 7/1992 | Cooper | E21B 49/00 250/253 |
| 5,548,115 A | * | 8/1996 | Ballard | E21B 47/01 250/253 |
| 5,639,956 A | * | 6/1997 | Christy | G01N 33/24 73/19.01 |
| 6,115,061 A | * | 9/2000 | Lieberman | E21B 47/0002 175/49 |
| 6,630,947 B1 | * | 10/2003 | Lieberman | E21B 47/0002 348/85 |
| 2008/0173804 A1 | * | 7/2008 | Indo | G01N 21/64 250/269.1 |
| 2013/0077830 A1 | * | 3/2013 | Liu | G06K 9/00818 382/104 |

(Continued)

*Primary Examiner* — David P Porta
*Assistant Examiner* — Gisselle M Gutierrez
(74) *Attorney, Agent, or Firm* — Jeffrey L. Thompson; Thompson Law, P.A.

(57) ABSTRACT

A soil imaging probe has a housing with an interior cavity and an outer surface exposed for sliding contact with soil. A window is mounted in the outer surface for providing optical communication between the soil and the interior cavity. An optical module is positioned within the interior cavity. The optical module includes at least one light source and a camera mounted in a block. An indexing surface is defined in the interior cavity to maintain the optical module at a predetermined fixed distance from the window to keep the camera focused on the soil outside the window. An elastomeric fill material fills the interior cavity and substantially surrounds the optical module to reduce energy transference from the housing of the probe to the optical module. An image processing method is also provided to identify pixels in an image captured by the camera that show potential hydrocarbon contamination.

23 Claims, 10 Drawing Sheets

(56) References Cited

U.S. PATENT DOCUMENTS

| | | | |
|---|---|---|---|
| 2016/0252650 A1* | 9/2016 | Hirst, Sr. | G01V 9/007 |
| | | | 348/143 |
| 2018/0045567 A1* | 2/2018 | Cabib | G01J 3/36 |
| 2019/0079011 A1* | 3/2019 | Frangioni | G01N 21/6428 |

\* cited by examiner

SOIL IMAGING PROBE AND METHOD OF PROCESSING SOIL IMAGE TO DETECT HYDROCARBON CONTAMINATION

RELATED APPLICATIONS

This application is a divisional of U.S. patent application Ser. No. 15/269,159 filed on Sep. 19, 2016, now U.S. Pat. No. 10,371,637, which claims the benefit of U.S. Provisional Patent Application No. 62/220,644 filed on Sep. 18, 2015. The entire contents of these related applications are incorporated herein by reference.

BACKGROUND OF THE INVENTION

Field of the Invention

The present invention relates generally to devices and methods for imaging and measuring contaminants in soil. In particular, the present invention relates to devices and methods for imaging and measuring contaminants in a bore hole using a camera mounted in a soil probe.

Description of the Related Art

Soil contamination is caused by the presence of chemicals, such as hydrocarbons, in the natural soil environment. Soil contamination can cause health risks from direct contact with the contaminated soil, vapors from the contaminants, and secondary contamination of water supplies within and underlying the soil.

Soil probing tools are commonly used for subsurface soil investigations to determine the presence and concentration of soil contaminants. For example, probing tools have been used to explore sites for hydrocarbon contamination in the soil.

Systems have been developed for logging soil properties in boreholes as probing tools are driven into or retracted from the ground. For example, U.S. Pat. No. 5,639,956 issued to Christy discloses a soil probe having a permeable membrane sensor disposed in the sidewall of the probe for sampling chemical compounds at different soil levels. Other types of sensors have also been placed on soil probes to measure and log properties of the soil at various levels as the probe is driven into or retracted from the soil.

Another example of a system for logging soil properties in a borehole using an imaging system is disclosed in U.S. Pat. Nos. 6,115,061 and 6,630,947 of Lieberman. Lieberman uses visible or UV light from a light source to illuminate the soil in the borehole, and a lens arrangement and imaging system for detecting light reflected back from the soil.

PCT Patent Application No. WO 2005/003728 of Rooney et al. discloses a soil probe with a light source for illuminating the soil in situ. The light source is cycled between multiple wavelengths for the colors red, blue and green, in succession. A photo-detector responsive to light of the various wavelengths is used to measure the color of the soil as an R-G-B measurement. Soil parameters are obtained by correlation with the soil color measurement.

U.S. Pat. No. 5,548,115 issued to Ballard et al. discloses a probe device for in-situ detection of contaminants in subsurface soil. The device uses UV light through a sapphire window to fluoresce contaminants in the soil.

U.S. Pat. No. 5,128,882 issued to Cooper discloses a soil probe for measuring reflectance and fluorescence of soil in situ. Reflected light is transmitted through a fiber optic link to the surface for measurement of spectral distribution and intensity.

There is a need in the industry for an improved soil imaging probe and method that uses a camera mounted in a soil probe to image and measure subsurface soil contaminants.

SUMMARY OF THE INVENTION

An object of the present invention is to provide a soil imaging probe that can be assembled in an efficient and economical manner.

A further object of the present invention is to provide a soil imaging probe that is configured in a manner to withstand percussion advancement of the probe.

A still further object of the present invention is to provide a soil imaging method that uses a two stage image filtering process to detect hydrocarbon contamination in the soil with reduced background detection.

These and other objects of the present invention are accomplished by a soil imaging probe having a housing with an interior cavity and an outer surface exposed for sliding contact with soil. A window is mounted in the outer surface for providing optical communication between the soil and the interior cavity. An optical module is positioned within the interior cavity. The optical module includes at least one light source and a camera mounted in a block. An indexing surface is defined in the interior cavity to maintain the optical module at a predetermined fixed distance from the window to keep the camera focused on the soil outside the window and properly aligned with the probe. An elastomeric fill material fills the interior cavity and substantially surrounds the optical module to reduce energy transference from the housing of the probe to the optical module. An image processing method is also provided to identify pixels in an image captured by the camera that show potential hydrocarbon contamination.

According to one aspect of the present invention, a soil imaging method is provided, comprising: acquiring an image of soil in a bore hole using a soil imaging probe having a window for providing optical communication between the soil and a camera positioned within the soil imaging probe; and processing the image to identify pixels in the image that show potential hydrocarbon contamination. The image processing comprises applying a first stage filter to the pixels that uses a first set of image parameters to assign a first fluorescence value to each pixel indicative of hydrocarbon contamination.

According to other aspects of the invention, the image processing further includes: applying a second stage filter to the pixels that uses a second set of image parameters to assign a second fluorescence value to each pixel indicative of hydrocarbon contamination; determining if the first stage filter detects fluorescence indicative of hydrocarbon contamination in at least a predetermined percentage of area of the image; and summing the first and second fluorescence values for use in visually rendering an image showing hydrocarbon contamination or for quantitatively describing a level of hydrocarbon contamination upon determining that the first stage filter detects fluorescence indicative of hydrocarbon contamination in at least the predetermined percentage of area of the image.

According to another aspect of the present invention, a soil imaging method is provided, comprising: acquiring an image of soil in a bore hole using a soil imaging probe having a window for providing optical communication between the soil and a camera positioned within the soil imaging probe; and processing the image to determine a percentage of area of the image that has fluorescence indicative of hydrocarbon contamination.

Numerous other objects of the present invention will be apparent to those skilled in this art from the following description wherein there is shown and described embodiments of the present invention, simply by way of illustration of some of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

Figure 1:
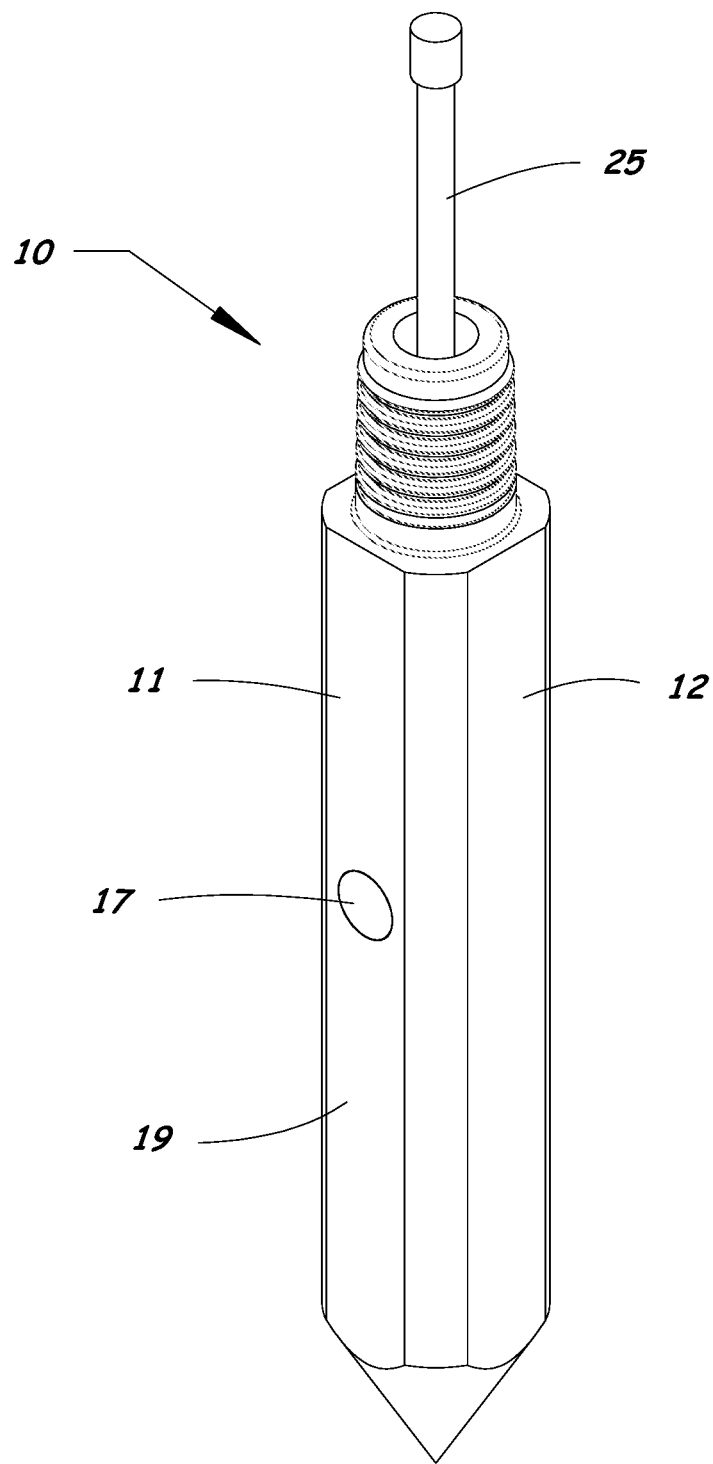
FIG. 1 is a perspective front view of a soil imaging probe according to the present invention.
Figure 2:
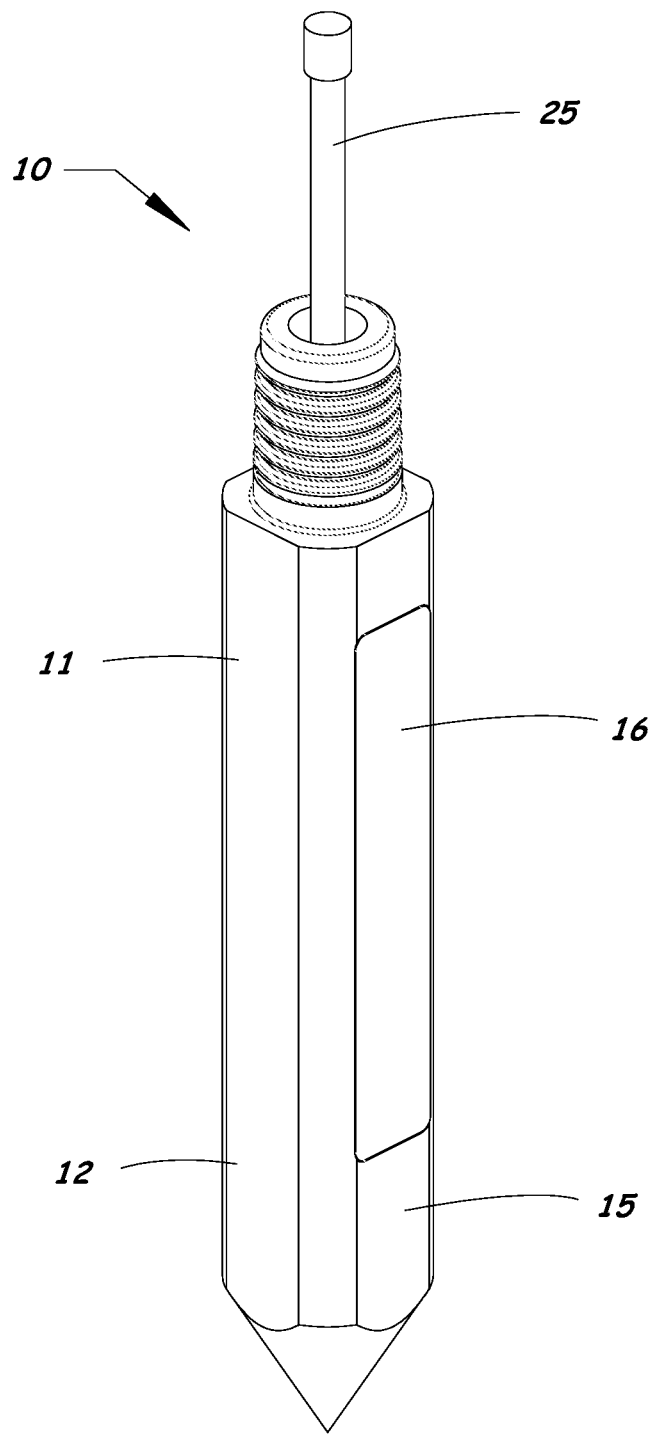
FIG. 2 is a perspective rear view of the soil imaging probe.
Figure 3:
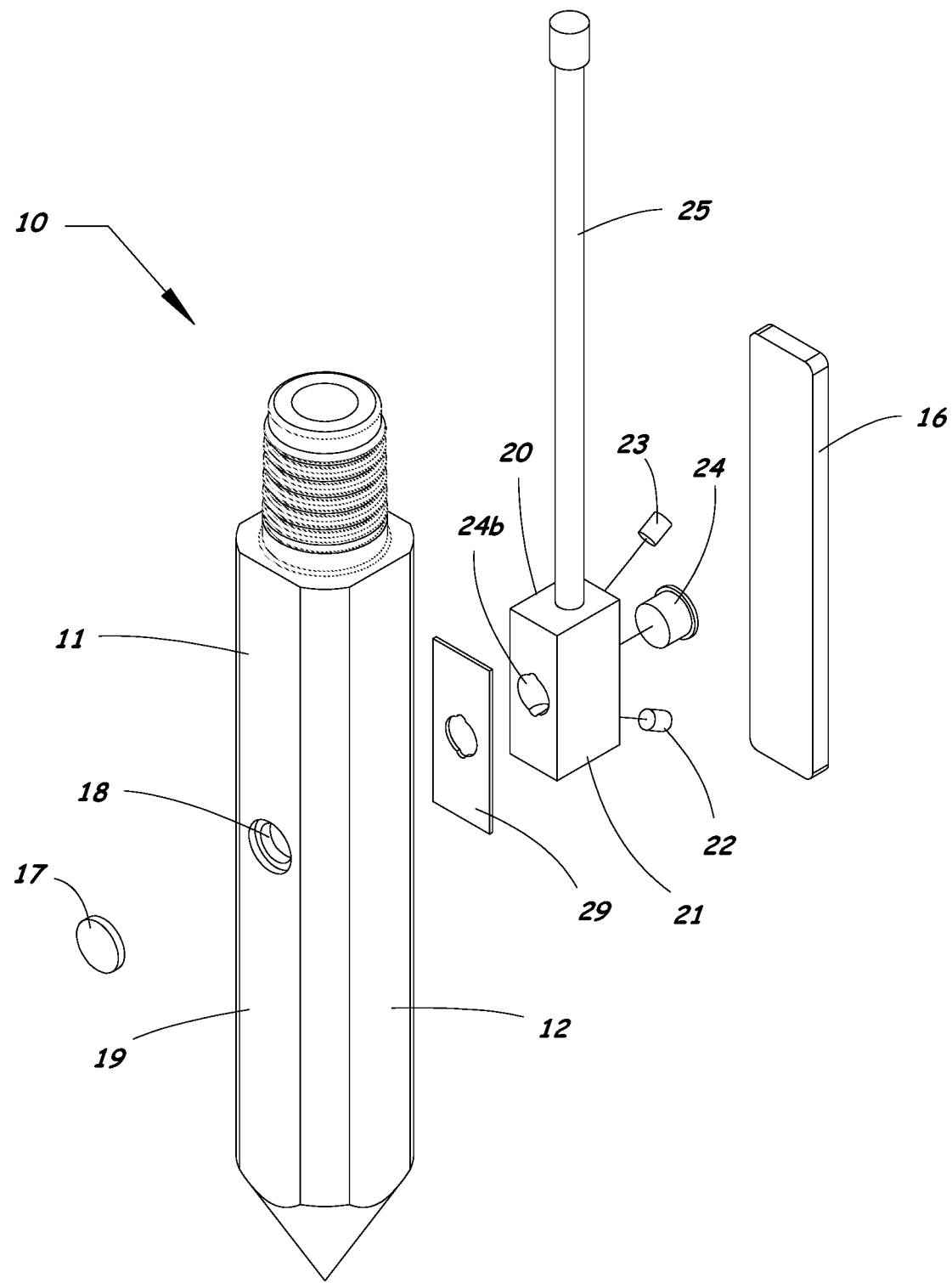
FIG. 3 is an exploded perspective front view of the soil imaging probe.
Figure 4:
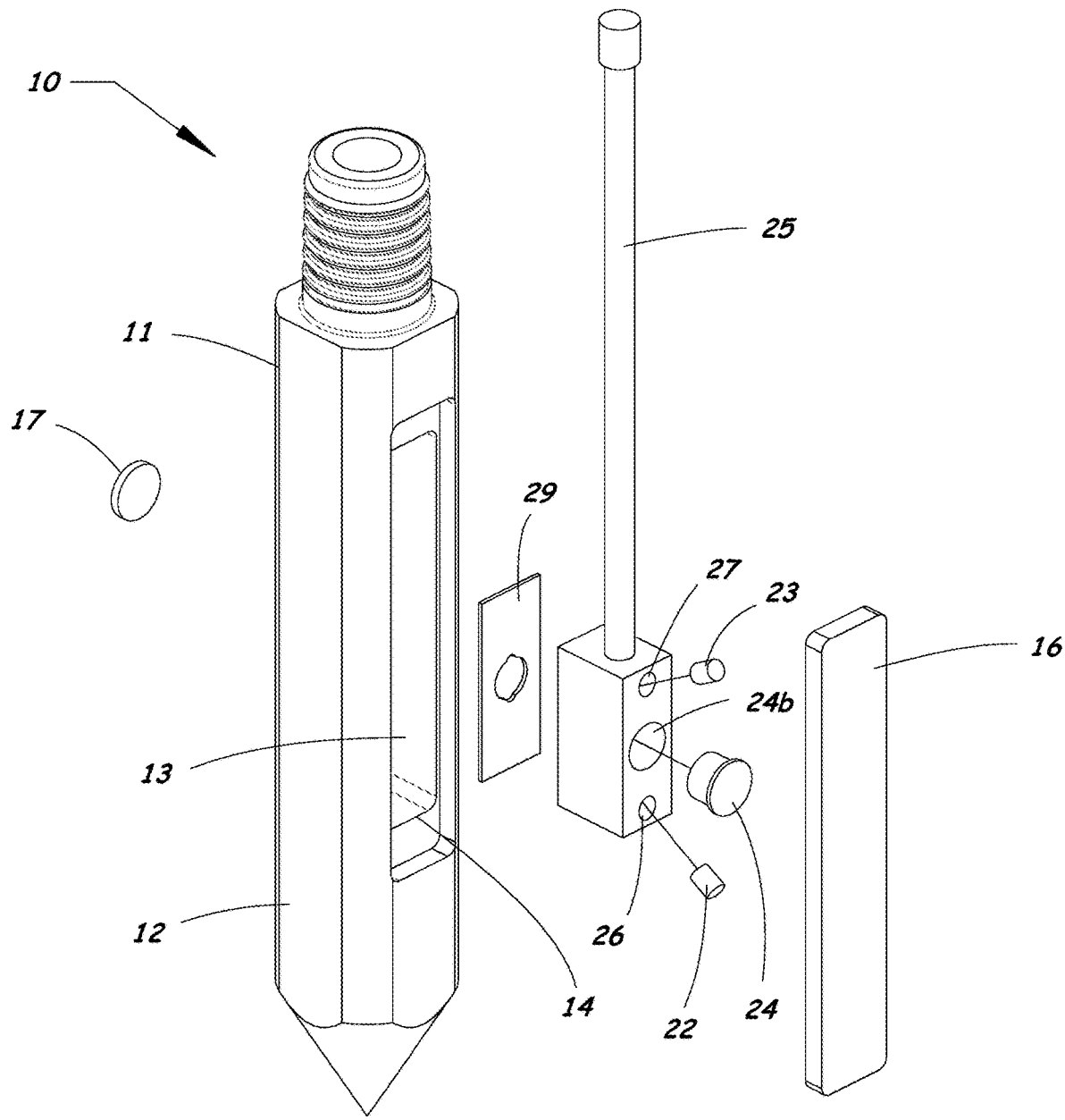
FIG. 4 is an exploded perspective rear view of the soil imaging probe.

A soil imaging probe 10 and soil imaging method according to the present invention will be described in detail with reference to FIGS. 1 to 12 of the accompanying drawings.

FIGS. 1 to 7 illustrate the soil imaging probe 10 of the present invention. The soil imaging probe 10 includes a housing 11 having a longitudinal axis and an outer surface 12 exposed for sliding contact with soil as the housing 11 is moved through the soil along its longitudinal axis. The housing 11 has an interior cavity 13. An access opening 14 is provided in a back side 15 of the housing 11, and an access cover 16 is provided to close the access opening 14 and seal the interior cavity 13. The access cover 16 is removable from the housing 11 to allow access through the access opening 14 to the interior cavity 13.

A window 17 is mounted in an opening 18 in the outer surface of a front side 19 of the housing 11 for providing optical communication between the soil and the interior cavity 13. The window 17 is preferably mounted flush with the exterior surface 12 of the probe 10 and made of a hard material, such as sapphire, to resist scratching as the probe 10 is driven into the soil. The window 17 is on the opposite side of the housing 11 from the access cover 16.

An optical module 20 is positioned within the interior cavity 13 of the housing 11. The optical module 20 includes a block 21, a pair of light sources 22, 23 mounted in the block 21, and a camera 24 mounted in the block 21. Also affixed to the block 21 are electrical components and electrical connections for the light sources 22, 23 and the camera 24 and other sensors (if any) contained within the probe 10. All of these components 22-24 are rigidly attached to the block 21. Electrical wires and gas lines (if used) can exit the block 21 as a single trunkline 25, which is directed out the top of the probe 10.

The block 21 is made of a rigid, lightweight material, such as aluminum or plastic. For example, the block 21 can be made of nylon, PVC, or ABS.

The light sources 22, 23 include a first light source 22 for emitting light having a first wavelength, and a second light source 23 for emitting light having a second wavelength different from the first wavelength. In one embodiment, the first light source 22 is a UV light source, and the second light source 23 is a visible light source.

The two light sources 22, 23 are fixed in respective bores 26, 27 in the block 21 that extend at an angle relative to each other and converge at a focal point located approximately at the external surface of the window 17. The camera 24 is fixed in a center bore 24b in the block 21 between the two light sources 22, 23 and aimed at the focal point.

During use, light is directed from the light sources 22, 23 to the soil through the window 17. Returning light from the soil returns back through the window 17 to the camera 24. The images captured by the camera 24 using this probe 10 can be either video or still. Images illuminated with visible light are used to view the soil present at the probe window 17. Images illuminated with UV light are used to detect the presence of certain hydrocarbon fuels that will fluoresce when exposed to UV excitation in the appropriate wavelengths. Images obtained with UV light are subjected to image processing, as described in detail below, to indicate the degree of fluorescence present in the soil and to separate hydrocarbon fluorescence from background mineral fluorescence.

An indexing surface 28 is provided on a front wall of the interior cavity 13. The indexing surface 28 is a planar surface that lies in a plane parallel to the longitudinal axis of the probe 10. The indexing surface 28 can be formed, for example, by machining the front wall of the interior cavity 13 through the access opening 14 so that a precise distance is created from the indexing surface 28 to the exterior surface of the window 17. The indexing surface 28 functions to maintain the optical module 20 at a predetermined fixed distance from the exterior surface of the window 17 to keep the camera 24 focused on the soil contacting the outside of the window 17 and properly aligned with the probe 10.

An elastomeric gasket 29 is positioned between the block 21 and the indexing surface 28 to isolate the optical module 20 from energy transference from the housing 11 to the optical module 20. For example, the elastomeric gasket 29 can be a of elastomeric material having a hardness of approximately Shore 30A, such as ⅛ inch thick silicone.

Figure 5:
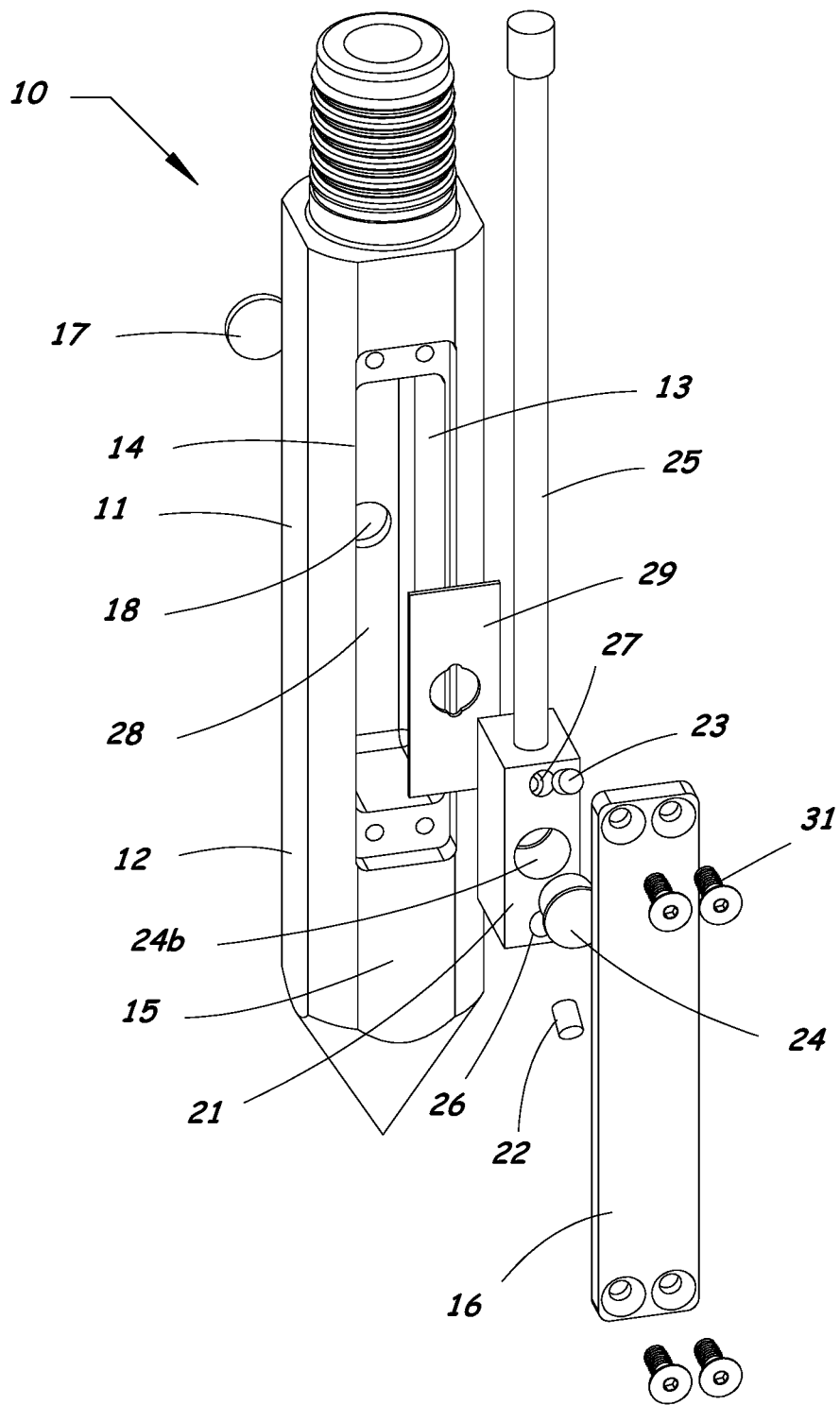
FIG. 5 is another exploded perspective rear view of the soil imaging probe.
Figure 6:
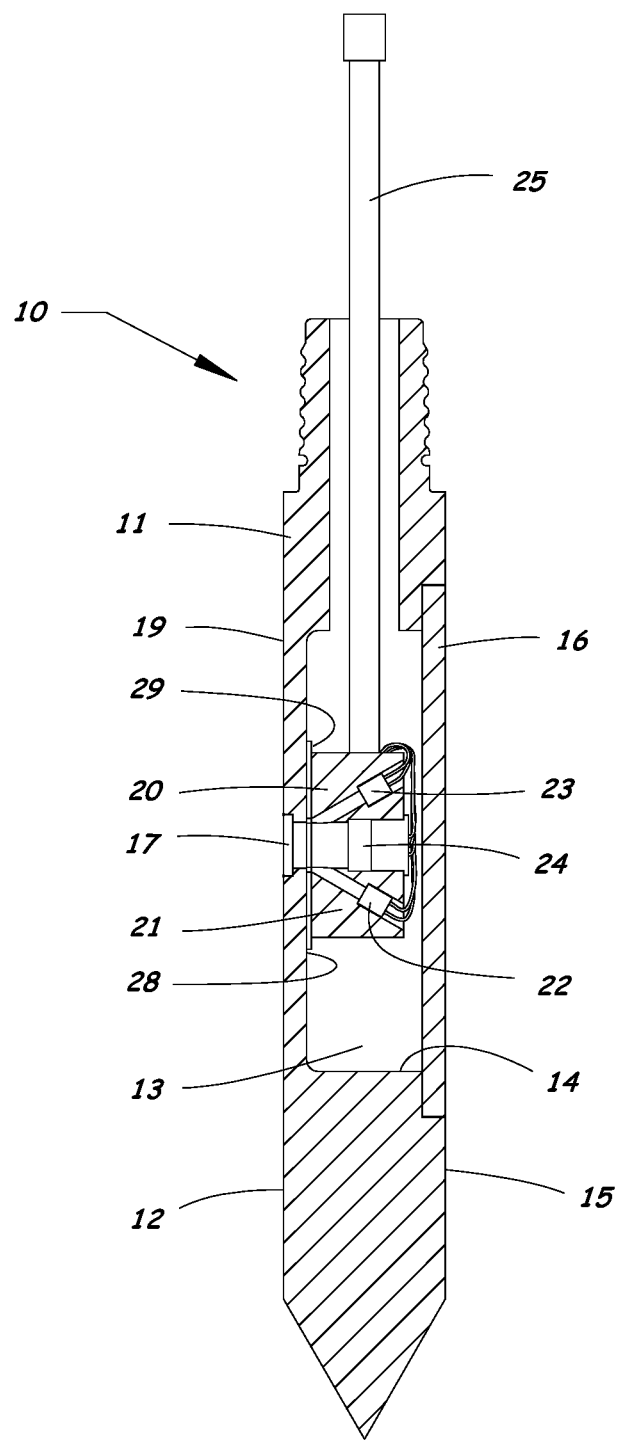
FIG. 6 is a cross section side view of the soil imaging probe.

As illustrated in FIGS. 5 and 6, the interior cavity 13 of the housing 11 is substantially longer than a longitudinal dimension of the block 21 of the optical module 20. For example, in the illustrated embodiment, the interior cavity 13 is more than 1.5 times as long as the longitudinal dimension of the block 21.

Figure 7:
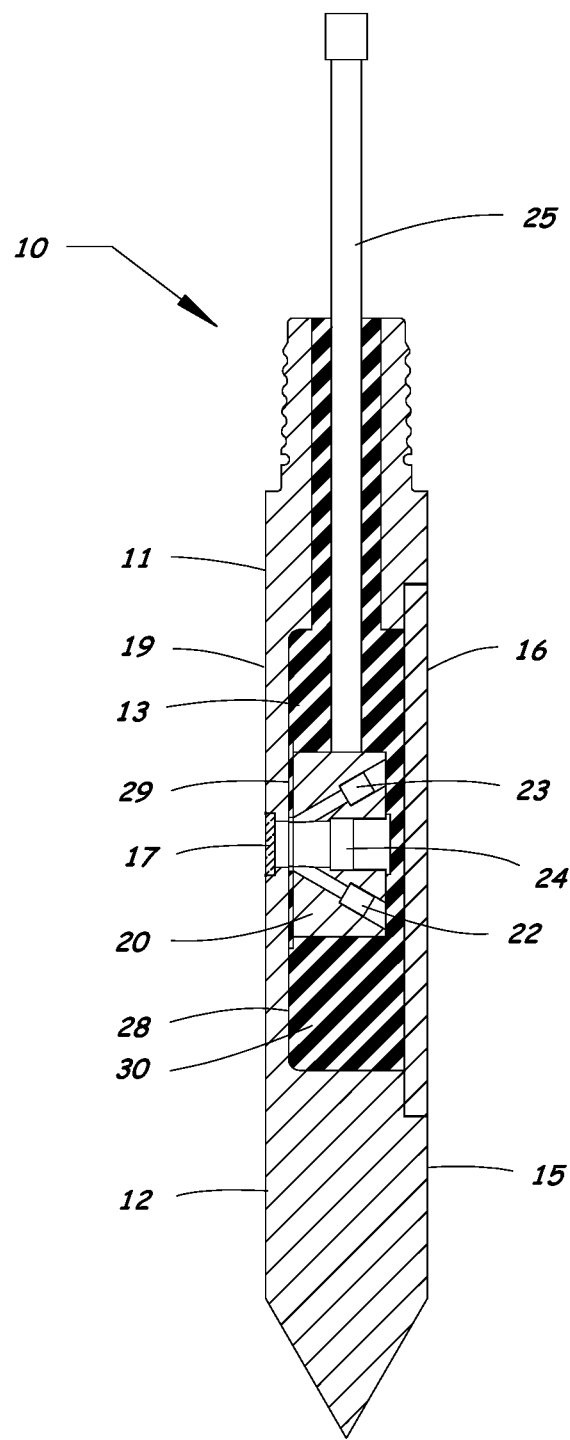
FIG. 7 is another cross section side view of the soil imaging probe showing an elastomeric fill material contained within an interior cavity of the probe.

As illustrated in FIG. 7, an elastomeric fill material 30 fills the interior cavity 13 of the housing 11 and substantially surrounds the optical module 20, except for the front side of the optical module 20 facing the indexing surface 28. The elastomeric fill material 30 functions to reduce energy transference from the housing 11 of the probe 10 to the optical module 20. Since the interior cavity 13 of the housing 11 is substantially longer than the optical module 20, the elastomeric fill material 30 effectively isolates the optical module 20 from the housing 11 of the probe 10 in a longitudinal direction. Thus, the elastomeric fill material 30 effectively isolates the optical module 20 from the severe energy forces imparted to the housing 11 in a longitudinal direction while driving the probe 10 into the soil.

The probe 10 is assembled by affixing the block 21 of the optical module 20 to the gasket 29, and the gasket 29 to the interior indexing surface 28 with a contact adhesive or other adhesive. Alternatively, no adhesive may be used and the block 21 and gasket 29 may be held against the interior indexing surface 28 by a temporary mechanical fastener inserted through the window opening 18.

The access cover 16 is secured to the housing using, for example, a plurality of threaded fasteners 31. The interior cavity 13 is then filled with an elastomeric fill material 30 initially in liquid form, such as silicone or polyurethane, that contacts and substantially surrounds the optical module 20 within the interior cavity 13. The elastomeric fill material 30 does not completely surround the optical module 20 because it does not reach the front side of the optical module 20, which is held against the gasket 29 and the indexing surface 28 during assembly to maintain the desired focal point for the camera 24 on the exterior surface of the window 17.

Once the elastomeric fill material 30 cures into its solid form, the optical module 20 is held in place against the indexing surface 28 by the elastomeric fill material 30 and can be released from its temporary hold through the window opening 18. The optical module 20 is thus held in place within the interior cavity 13 only by the elastomeric fill material 30 and without the use of any rigid mechanical fastening. In other words, the optical module 20 is free floating within the elastomeric fill material 30 in the interior cavity 13. The elastomeric fill material 30 cushions the optical module 20 and prevents percussive energy used to drive the probe 10 into the soil from damaging the components 20-23 of the optical module 20. Within the confines of the elastomeric fill material 30, the optical block 20 is free to move relative to the indexing surface 28 in a longitudinal direction.

The soil imaging probe 10 described above allows the camera 24, light sources 22, 23, and other electronic components to be fixed to a single rigid block 21 of lightweight material. This block 21 can be placed in the interior cavity 13 of the probe housing 11 through the access opening 14, indexed to the window 17 of the probe 10 by the indexing surface 28, and held in place with the elastomeric fill material 30. Within the elastomeric fill material 30, the block 21 is free floating, not being fixed to the probe 10 with any rigid mechanical fastening.

A soil image processing method according to the present invention will now be described with reference to FIGS. 8 to 12. The soil image processing method can be used to indicate the degree of fluorescence present in the soil and to separate hydrocarbon fluorescence from background mineral fluorescence.

Figure 8:
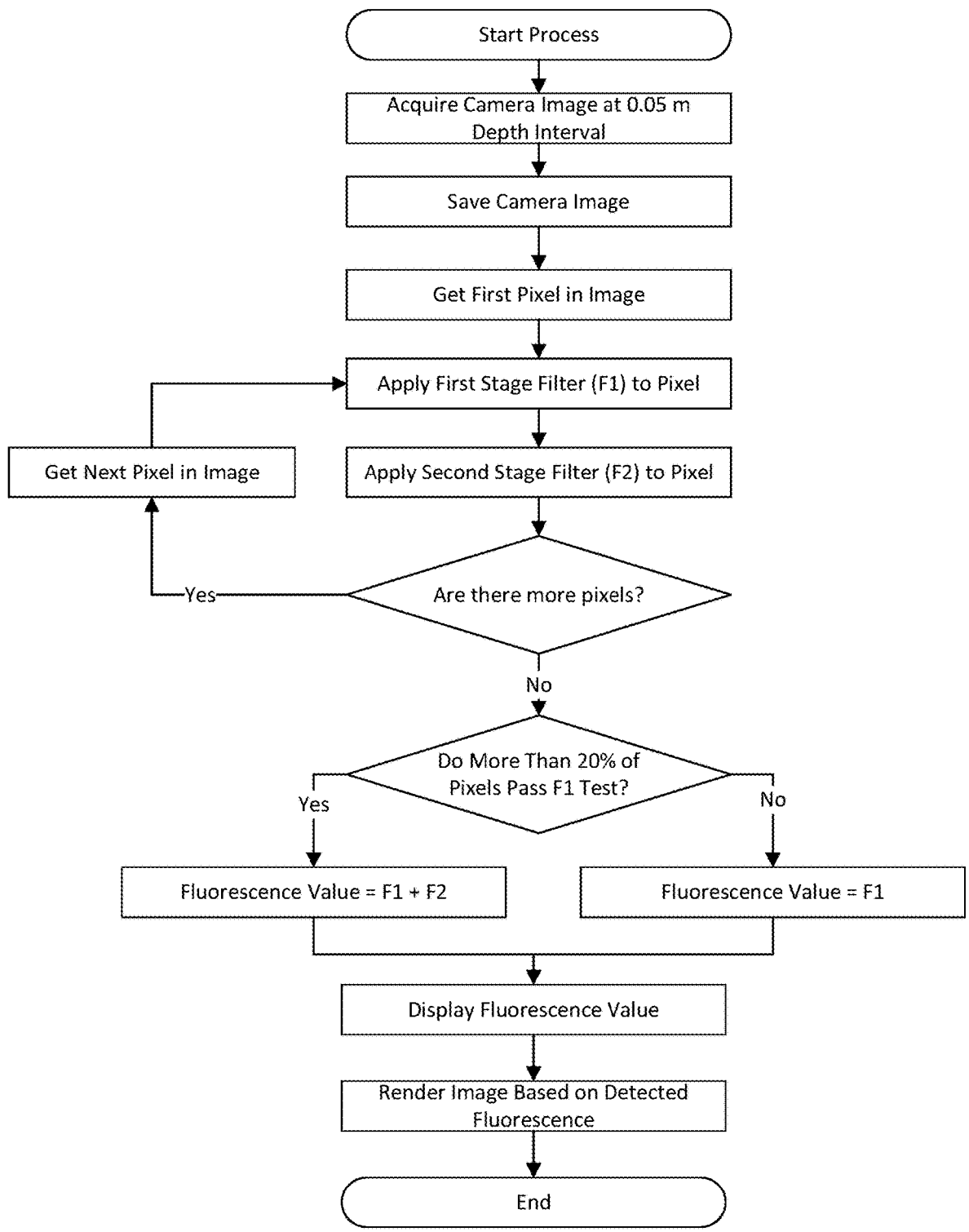
FIG. 8 is a flow chart showing a soil imaging method of the present invention that uses a two-stage filtering process to determine fluorescence indicative of soil contamination.

FIG. 8 is a flow chart of the soil imaging method used to determine fluorescence indicative of soil contamination. An image of soil in a bore hole is acquired using a soil imaging probe having a window for providing optical communication between the soil and a camera positioned within the soil imaging probe. For example, the soil imaging probe 10 described above can be used to acquire the soil images used in this soil image processing method.

The soil imaging probe 10 is used to acquire digital camera images of soil under UV illumination at fixed increments (e.g., 0.05 ft) as the probe 10 is advanced in the soil. These camera images are then analyzed to determine what area of the image emits light indicative of hydrocarbon fuel fluorescence. More specifically, each acquired digital camera image is processed to identify pixels in the image that show potential hydrocarbon contamination. The result of the image processing is used to generate a fluorescence value for use in visually rendering an image showing hydrocarbon contamination, or for quantitatively describing a level of hydrocarbon contamination.

The image processing uses a two stage filtering process designed to identify hydrocarbon contamination signals and to separate those signals from background soil fluorescence and reflectance. In this filtering process, Hue, Saturation, and Value (HSV) color filters are applied to each pixel in the soil image. Pixels that indicate positive for fluorescence in this analysis can then be represented either through a visually rendered image or quantitatively described by the percent area of the image. The quantitative description can also use a factor for the intensity of light in the area of fluorescence.

The image processing applies a first stage filter to the pixels using a first set of image parameters to assign a first fluorescence value to each pixel indicative of hydrocarbon contamination. The first stage filter identifies pixels having a Hue range and a first brightness Value range indicative of hydrocarbon fluorescence, and having a first Saturation range. The first stage filter is set to identify pixels that are high in color in the Hue range typical of hydrocarbon fluorescence and are of sufficient brightness to indicate hydrocarbon contamination. The first stage filter does not detect high concentrated areas of product near the center of a fluorescent image. For example, the first stage filter can be set to identify pixels having a Hue range of approximately 150 to 220, a Saturation range of approximately 127 to 255, and a brightness Value range of approximately 105 to 255.

The image processing applies a second stage filter to the pixels using a second set of image parameters to assign a second fluorescence value to each pixel indicative of hydrocarbon contamination. The second stage filter identifies image pixels low in color and high in brightness; a condition typical of high fluorescence in certain hydrocarbons, as well as a condition found at the center of many images with strong fluorescence values identified by the first stage filter. The second stage filter identifies pixels having, for example, the same Hue range as the first stage filter, a second brightness Value range, and a second Saturation range. The second brightness Value range has a lower limit that is higher than a lower limit of the first brightness Value range. The second Saturation range is lower than the first Saturation range. For example, the second stage filter can be set to identify pixels having a Hue range of approximately 150 to 220, a Saturation range of approximately 0 to 127, and a brightness Value range of approximately 150 to 255.

The second stage filter uses Saturation levels below a lower limit of the first stage filter to detect hydrocarbon contamination indicated by fluorescent light of low color and high brightness. This condition often occurs in soil images made in zones with high hydrocarbon concentrations and most often is found near the center of soil images. The second stage filter uses brightness Values above a lower limit of the first stage filter to decrease background detection caused by low Saturation parameter limits.

The image processing determines if the first stage filter detects fluorescence indicative of hydrocarbon contamination in at least a predetermined percentage of area of the image. For example, the predetermined percentage can be approximately 20% of the area of the image.

If the first stage filter detects fluorescence indicative of hydrocarbon contamination in less than the predetermined percentage of area of the image, then the first fluorescence value is output for use in visually rendering an image showing hydrocarbon contamination, or for use in quantitatively describing the level of hydrocarbon contamination.

If the first stage filter detects fluorescence indicative of hydrocarbon contamination in more than the predetermined percentage of area of the image, then the first fluorescence value is summed with the second fluorescence value for use in visually rendering an image showing hydrocarbon contamination, or for use in quantitatively describing the level of hydrocarbon contamination. The second fluorescence value is only summed with the first fluorescence value if the first stage filter detects fluorescence in at least the predetermined percentage of the image to avoid background detections from soil minerals having low color.

The fluorescence value output by the image processing algorithm is used to display a quantitative description of a level of hydrocarbon contamination based on the percentage of area of the image determined to have fluorescence indicative of hydrocarbon contamination. The quantitative description can include a factor for the intensity of light in a fluorescing area of the image.

The fluorescence value output by the image processing algorithm can also be used to render a visual image to show detected hydrocarbon contamination. The rendered image includes a visual indication of hydrocarbon contamination for each pixel in the image. The visual indication is based only on the first fluorescence value when the first stage filter detects fluorescence in less than the predetermined percentage of area of the image, and is based on the sum of the first and second fluorescence values when the first stage filter detects fluorescence in more than the predetermined percentage of area of the image.

Figure 9:
FIG. 9 shows a raw image of typical uncontaminated soil in a bore hole.
Figure 10:
FIG. 10 shows a raw image of contaminated soil in a bore hole.
Figure 11:
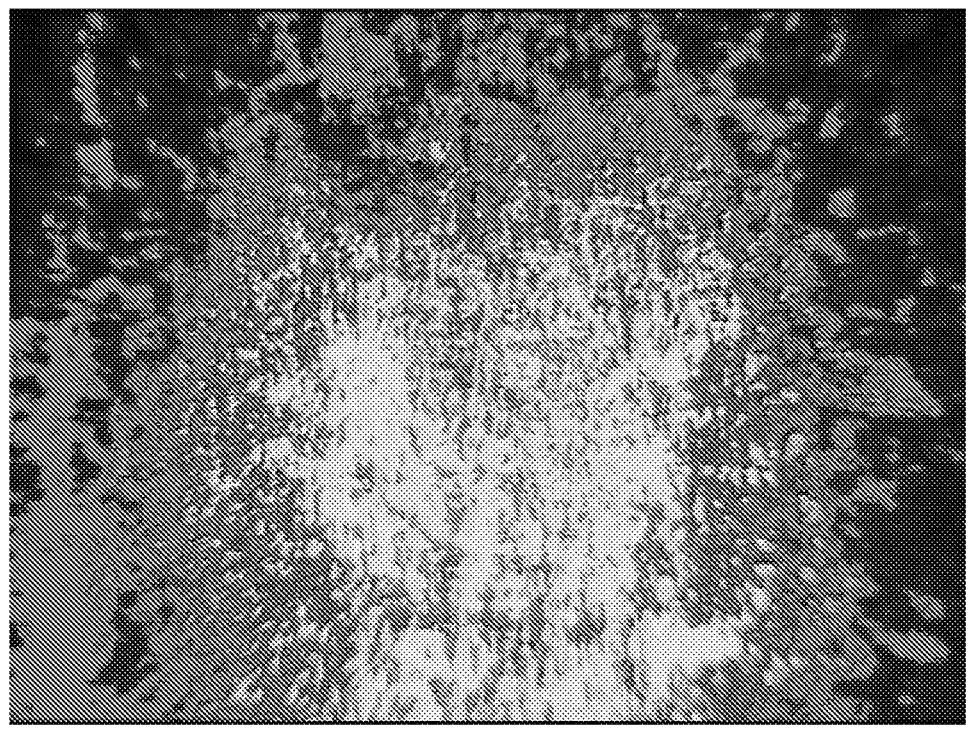
FIG. 11 shows a rendered image of the soil shown in FIG. 10, with the pixels passing a first stage filter shown in red.
Figure 12:
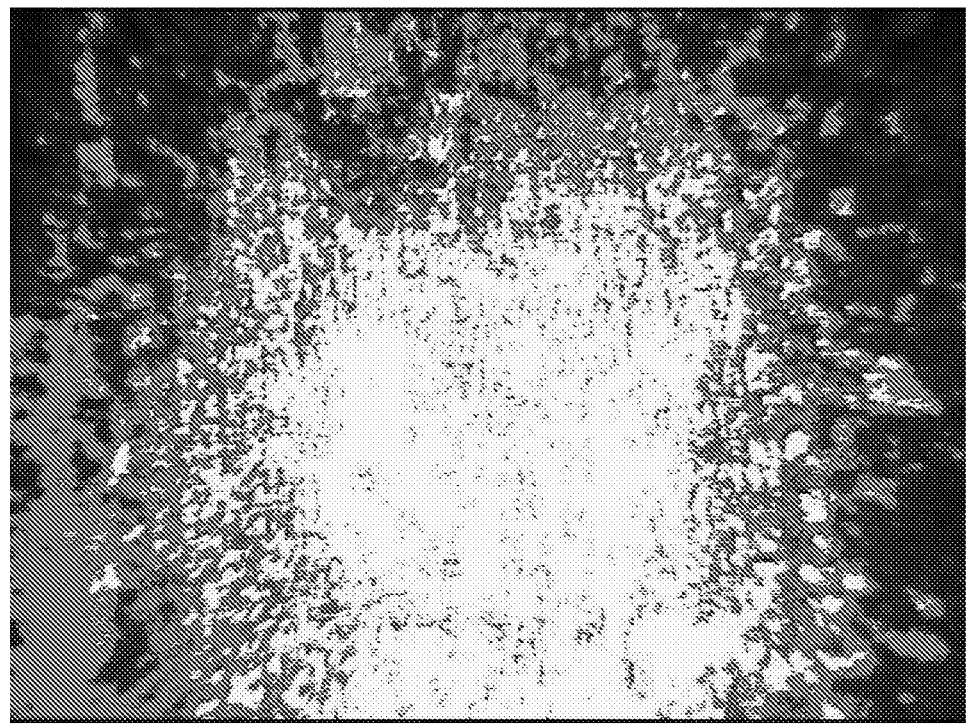
FIG. 12 shows a rendered image of the soil shown in FIG. 10, with the pixels passing a second stage filter shown in yellow.

FIGS. 9 to 12 further illustrate the image analysis process used in the present invention. FIGS. 9 and 10 show raw images of soil obtained at different depths within the same bore hole. FIGS. 11 and 12 show images with rendered pixels from the image analysis process.

FIG. 9 shows a raw image of soil from a first depth in the bore hole. This image is typical of background, uncontaminated, soils. The image exhibits low fluorescence and yields a fluorescence value of approximately 0% from the image analysis process.

FIG. 10 shows another raw image of soil from a second depth in the bore hole. This image was obtained in a hydrocarbon contaminated zone and contains visually discernible hydrocarbon fluorescence.

FIG. 11 shows a rendered image of the soil shown in FIG. 10, with the pixels passing the first stage filter shown in red. The total area passing the first stage filter is approximately 29.7% in this image.

The image from FIG. 11 has sufficient fluorescent area identified by the first stage filter to use the fluorescence value output from the second stage filter. Pixels passing the second stage filter are shown in yellow in FIG. 12. The area passing the second stage filter is approximately 36.2% in this image. This area is summed to the area detected by the first stage filter to yield a fluorescence area value of approximately 65.9% for this image.

Filter parameters for the first and second stage filters of the image processing can be determined through test comparisons of soils with and without hydrocarbon contamination. For example, several sample soil types can be contaminated with known quantities of hydrocarbons and compared to non-contaminated control samples. Hue parameters can be determined by examining fluorescence of several types of hydrocarbons at low concentrations up to free product concentrations. Hue can be selected to span just beyond the maximum and minimum limits of the fluorescent Hues detected in the samples. Saturation and Value parameters can be set based on the comparisons of the images of the contaminated soils and the uncontaminated control soils.

The parameters for the first and second stage filters are set such as to minimize background detection while maximizing detection of hydrocarbon contamination. The parameters for the second stage filter are selected based on free product tests. Free product near the focus of the camera image produces high fluorescence of light with Saturation levels below the first stage filter detection limits. The Value parameters of the second stage filter are set sufficiently high to exclude background detection that could be caused by soil reflection or fluorescence of soil minerals.

The image analysis process described above applies both the first and second stage filters to each pixel of an image before determining whether the first stage filter detects fluorescence in at least the predetermined percentage of area of the image. However, it will be appreciated that the image analysis process could be modified so that the second stage filter is only applied to the pixels in an image if the first stage filter detects fluorescence in at least the predetermined percentage of area of the image. In this modified process, the fluorescence value output from the image analysis process would be the same as in the process described above and shown in FIG. 8, the only difference being that the second stage filter would only be applied to the pixels in an image if the threshold level of fluorescence is first detected by the first stage filter.

While the invention has been described in connection with specific embodiments thereof, it is to be understood that this is by way of illustration and not of limitation, and the scope of the appended claims should be construed as broadly as the prior art will permit.

What is claimed is:

1. A soil imaging method, comprising:
    acquiring a digital camera image of soil in a bore hole using a soil imaging probe having a window for providing optical communication between the soil and a camera positioned within said soil imaging probe, said digital camera image comprising a plurality of pixels; and
    processing said digital camera image to identify pixels in the digital camera image that show potential hydrocarbon contamination, wherein said image processing comprises applying a first stage filter to each of said pixels that uses a first set of image parameters to assign a first fluorescence value to each pixel indicative of hydrocarbon contamination.

2. The soil imaging method according to claim 1, wherein said image processing further comprises using the first fluorescence value in visually rendering an image showing hydrocarbon contamination or for quantitatively describing a level of hydrocarbon contamination.

3. The soil imaging method according to claim 1, wherein said image processing further comprises applying a second stage filter to said pixels that uses a second set of image parameters to assign a second fluorescence value to each pixel indicative of hydrocarbon contamination.

4. The soil imaging method according to claim 3, wherein said image processing further comprises determining if the first stage filter detects fluorescence indicative of hydrocarbon contamination in at least a predetermined percentage of area of the image.

5. The soil imaging method according to claim 1, further comprising rendering a visual image based on said image processing to show detected hydrocarbon contamination.

6. The soil imaging method according to claim 5, wherein said rendered image includes a visual indication of hydrocarbon contamination for each pixel.

7. The soil imaging method according to claim 6, wherein said visual indication is based on said first fluorescence value when said first stage filter detects fluorescence in less than said predetermined percentage of area of the image.

8. The soil imaging method according to claim 3, further comprising rendering a visual image based on said image processing to show detected hydrocarbon contamination, wherein said rendered image includes a visual indication of hydrocarbon contamination for each pixel, wherein said visual indication is based on said first fluorescence value when said first stage filter detects fluorescence in less than said predetermined percentage of area of the image, and wherein said visual indication is based on the sum of said first and second fluorescence values when said first stage filter detects fluorescence in more than said predetermined percentage of area of the image.

9. The soil imaging method according to claim 1, further comprising displaying a quantitative description of a level of hydrocarbon contamination based on a percentage of area of the image determined to have fluorescence indicative of hydrocarbon contamination.

10. The soil imaging method according to claim 9, wherein said quantitative description includes a factor for the intensity of light in a fluorescing area of the image.

11. The soil imaging method according to claim 3, wherein said second stage filter uses Saturation levels below a lower limit of said first stage filter to detect free product hydrocarbon contamination near a focus of the camera image.

12. The soil imaging method according to claim 3, wherein said second stage filter uses brightness Values above a lower limit of said first stage filter to decrease background detection caused by low Saturation parameter limits.

13. A soil imaging method, comprising:
acquiring an image of soil in a bore hole using a soil imaging probe having a window for providing optical communication between the soil and a camera positioned within said soil imaging probe; and
processing said image to identify pixels in the image that show potential hydrocarbon contamination, wherein said image processing comprises applying a first stage filter to said pixels that uses a first set of image parameters to assign a first fluorescence value to each pixel indicative of hydrocarbon contamination;
wherein said image processing further comprises applying a second stage filter to said pixels that uses a second set of image parameters to assign a second fluorescence value to each pixel indicative of hydrocarbon contamination;
wherein said image processing further comprises determining if the first stage filter detects fluorescence indicative of hydrocarbon contamination in at least a predetermined percentage of area of the image;
wherein said image processing further comprises summing the first and second fluorescence values for use in visually rendering an image showing hydrocarbon contamination or for quantitatively describing a level of hydrocarbon contamination upon determining that the first stage filter detects fluorescence indicative of hydrocarbon contamination in at least said predetermined percentage of area of the image.

14. The soil imaging method according to claim 13, wherein said second fluorescence value is only summed with said first fluorescence value if the first stage filter detects fluorescence in at least said predetermined percentage of the image to avoid background detections from soil minerals having low color.

15. A soil imaging method, comprising:
acquiring an image of soil in a bore hole using a soil imaging probe having a window for providing optical communication between the soil and a camera positioned within said soil imaging probe; and
processing said image to identify pixels in the image that show potential hydrocarbon contamination, wherein said image processing comprises applying a first stage filter to said pixels that uses a first set of image parameters to assign a first fluorescence value to each pixel indicative of hydrocarbon contamination;
wherein said image processing further comprises applying a second stage filter to said pixels that uses a second set of image parameters to assign a second fluorescence value to each pixel indicative of hydrocarbon contamination; and
wherein said first stage filter identifies pixels having a Hue range and a first brightness Value range indicative of hydrocarbon fluorescence, and having a first Saturation range.

16. The soil imaging method according to claim 15, wherein said second stage filter identifies pixels having said Hue range, a second brightness Value range, and a second Saturation range.

17. The soil imaging method according to claim 16, wherein said second brightness Value range has a lower limit that is higher than a lower limit of said first brightness Value range, and said second Saturation range is lower than said first Saturation range.

18. The soil imaging method according to claim 16, wherein said first stage filter identifies pixels having a Hue range of approximately 150 to 220.

19. The soil imaging method according to claim 16, wherein said first stage filter identifies pixels having a Saturation range of approximately 127 to 255.

20. The soil imaging method according to claim 16, wherein said first stage filter identifies pixels having a brightness Value range of approximately 105 to 255.

21. The soil imaging method according to claim 16, wherein said second stage filter identifies pixels having a Hue range of approximately 150 to 220.

22. The soil imaging method according to claim 16, wherein said second stage filter identifies pixels having a Saturation range of approximately 0 to 127.

23. The soil imaging method according to claim 16, wherein said second stage filter identifies pixels having a brightness Value range of approximately 150 to 255.

* * * * *